United States Patent
Zolotukhin et al.

(10) Patent No.: US 11,103,556 B2
(45) Date of Patent: *Aug. 31, 2021

(54) SATIATION PEPTIDE ADMINISTRATION

(71) Applicant: University of Florida Research Foundation, Incorporated, Gainesville, FL (US)

(72) Inventors: Sergei Zolotukhin, Gainesville, FL (US); Andres Acosta, Rochester, MN (US)

(73) Assignee: University of Florida Research Foundation, Incorporated, Gainesville, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/562,382

(22) Filed: Sep. 5, 2019

(65) Prior Publication Data

US 2020/0061158 A1 Feb. 27, 2020

Related U.S. Application Data

(60) Continuation of application No. 15/271,369, filed on Sep. 21, 2016, which is a division of application No. 13/145,660, filed as application No. PCT/US2010/021677 on Jan. 21, 2010, now Pat. No. 9,492,505.

(60) Provisional application No. 61/146,287, filed on Jan. 21, 2009.

(51) Int. Cl.
| | |
|---|---|
| *A61K 38/22* | (2006.01) |
| *C07K 14/575* | (2006.01) |
| *A61K 9/00* | (2006.01) |
| *A61K 48/00* | (2006.01) |
| *A61K 9/68* | (2006.01) |

(52) U.S. Cl.
CPC .............. *A61K 38/22* (2013.01); *A61K 9/006* (2013.01); *A61K 9/0019* (2013.01); *A61K 9/0056* (2013.01); *A61K 9/0058* (2013.01); *A61K 48/005* (2013.01); *A61K 48/0075* (2013.01); *C07K 14/575* (2013.01); *C12N 2799/025* (2013.01)

(58) Field of Classification Search
CPC .. A61K 9/0053; A61K 9/0019; A61K 9/0056; A61K 9/006; A61K 48/005; A61K 48/0075; A61K 38/22; A61K 9/0058; A61K 9/06; C07K 14/575
See application file for complete search history.

(56) References Cited

U.S. PATENT DOCUMENTS

| | | |
|---|---|---|
| 4,671,953 A | 6/1987 | Stanley et al. |
| 5,912,227 A | 6/1999 | Croom, Jr. et al. |
| 6,106,844 A | 8/2000 | King |
| 6,177,096 B1 * | 1/2001 | Zerbe ............... A61K 8/0208 424/435 |
| 6,998,387 B1 | 2/2006 | Goke et al. |
| 7,459,432 B2 | 12/2008 | Cowley et al. |
| 8,058,233 B2 | 11/2011 | Cowley et al. |
| 8,202,836 B2 | 6/2012 | Moore et al. |
| 8,273,713 B2 | 9/2012 | Pittner et al. |
| 9,492,505 B2 | 11/2016 | Zolotukhin et al. |
| 2004/0086579 A1 | 5/2004 | Higgins et al. |
| 2005/0009748 A1 | 1/2005 | Dinh et al. |
| 2006/0014678 A1 | 1/2006 | Cowley et al. |
| 2007/0275893 A1 | 11/2007 | Quay |
| 2008/0015265 A1 | 1/2008 | Rubin et al. |
| 2008/0254108 A1 | 10/2008 | Rosenberg |
| 2009/0004224 A1 | 1/2009 | Steward et al. |
| 2011/0070287 A1 | 3/2011 | Nielsen et al. |
| 2011/0092416 A1 | 4/2011 | Doyle et al. |
| 2012/0035100 A1 | 2/2012 | Zolotukhin et al. |
| 2014/0199272 A1 | 7/2014 | Chiorini et al. |
| 2017/0080056 A1 | 3/2017 | Zolotukhin et al. |
| 2017/0326257 A1 | 11/2017 | Zolotukhin et al. |
| 2019/0224280 A1 | 7/2019 | Acosta et al. |
| 2019/0231850 A1 | 8/2019 | Acosta et al. |

FOREIGN PATENT DOCUMENTS

| | | |
|---|---|---|
| WO | WO 2003/026591 A2 | 4/2003 |
| WO | WO 2003/057170 A2 | 7/2003 |
| WO | WO 2005/080433 A2 | 9/2005 |
| WO | WO 2005/110467 A1 | 11/2005 |
| WO | WO 2008/109068 A2 | 9/2008 |
| WO | WO 2017/009236 A2 | 1/2017 |

OTHER PUBLICATIONS

International Search Report and Written Opinion for International Application No. PCT/US2010/021677 dated Oct. 22, 2010.
International Preliminary Report on Patentability for International Application No. PCT/US2010/021677 dated Aug. 4, 2011.
Baggio et al., Oxyntomodulin and glucagon-like peptide-1 differentially regulate murine food intake and energy expenditure. Gastroenterology. Aug. 2004;127(2):546-58.
Fagoe et al., A compact dual promoter adeno-associated viral vector for efficient delivery of two genes to dorsal root ganglion neurons. Gene Ther. Mar. 2014;21(3):242-52. doi: 10.1038/gt.2013.71. Epub Nov. 28, 2013.
Fazen, et al. "Oral Delivery of the Appetite Suppressing Peptide hPYY(3-36) through the Vitamin B12 Uptake Pathway"; J. Med. Chem; 2011; 54(24) 8707-8711.
Hurtado, et al.; "Salivary Peptide Tyrosine-Tyrosine 3-36 Modulates INgestive Behavior without Inducing Taste Aversion"; The Journal of Neuroscience; 2013; 33(47) 18368-18380.

(Continued)

*Primary Examiner* — Gregory S Emch
(74) *Attorney, Agent, or Firm* — Wolf, Greenfield & Sacks, P.C.

(57) ABSTRACT

Disclosed herein are compositions and methods for treating obesity involving satiation gut peptide administration to the mouth of a subject for a predetermined dose and frequency. In other embodiments, materials and methods of treating certain psychological disorders are disclosed involving satiation gut peptides. In exemplary embodiments, the satiation gut peptide pertains to PYY.

27 Claims, 6 Drawing Sheets

Specification includes a Sequence Listing.

(56) References Cited

OTHER PUBLICATIONS

Steinert et al. "Oral administration of glucagon-like peptide 1 or peptide YY 3-36 affects food intake in healthy male subjects 1-3"; Am J. Clin Nutr; 2010; 92: 810-817.

Wank. S.A. G Protein-coupled receptors in gastrointestinal physiology I. CCK receptors: an exemplary family. Am. J. Physiol., 1998, vol. 274 (Gastrointest. Liver Physiol), pp. G607-G613.

Moran et al., Cholecystokinin suppresses food intake by inhibiting gastric emptying. Am J Physiol. May 1982;242(5):R491-7.

Underwood, Salivary gland biopsy. Healthline. Jan. 4, 2016;9 pages. Retrieved from the internet: <https://www.healthline.com/health/salivary-gland-biopsy>. Last accessed on Apr. 3, 2020.

Gupta, Glucagon-like peptide-1 analogues: An overview. Indian J Endocrinol Metab. May 2013;17(3):413-21. doi: 10.4103/2230-8210.111625.

* cited by examiner

FIG. 6 a) SEQ. ID NO. 1 (Human Peptide YY amino acid sequence)

i) MVFVRRPWPA LTTVLLALLV CLGALVDAYP IKPEAPGEDA SPEELNRYYA
SLRHYLNLVT RQRYGKRDGP DTLLSKTFFP DGEDRPVRSR SEGPDLW     ii) MVFVRRPWPALTTVLLALLVCLGALVDAYPIKPEAPREDASPEE
        LNRYYASLRHYLNLVTRQRYGKRDGPDTLLSKTFFPDGEDRPVRSRSEGPDLW

SEQ ID NO. 9 b) SEQ ID NO. 2 (Human Peptide YY 3-36 amino acid sequence)

IKPEAPGEDA SPEELNRYYA SLRHYLNLVT RQRY

"Isolation and primary structure of human peptide YY." Tatemoto K., Nakano I., Makk G., Angwin P., Mann M., Schilling J., Go V.L.W. Biochem. Biophys. Res. Commun. 157:713-717(1988); "A new molecular form of PYY: structural characterization of human PYY(3-36) and PYY(1-36)." Eberlein G.A., Eysselein V.E., Schaeffer M., Layer P., Grandt D., Goebell H., Niebel W., Davis M., Lee T.D., Shively J.E., Reeve J.R. Jr. Peptides 10:797-803(1989); "Cloning and structural determination of human peptide YY cDNA and gene.", Kohri K., Nata K., Yonekura H., Nagai A., Konno K., Okamoto H. Biochim. Biophys. Acta 1173:345-349(1993) (discloses nucleotide sequence)

c) SEQ ID NO. 3 (Oxyntomodulin, human)

HSQGTFTSDYSKYLDSRRAQDFVQWLMNTKRNKNNIA

WO/2007/100535 and WO/2005/035761 d) Glucagon-like Peptide 1: U.S. Patent Nos, 5631224, 6191102, and 6998387.

e) cholecystokinin:

SEQ ID NO. 4: (homo sapiens)
MNSGVCLCVLMAVLAAGALTQPVPPADPAGSGLQRAEEAPRRQLRVSQRTDGESRAHLGALLA
RYIQQARKAPSGRMSIVKNLQNLDPSHRISDRDYMGWMDFGRRSAEEYEYPS SEQ ID NO. 5 (homo sapiens-full cDNA)
```
  1  cacttcaacc ggttgtcgcc ccagtggccg ccctctgagc acgtgttact gccagtctgc
 61  gtcagcgttg ggtaaataca tgactggccg acgccgccgg gcggggctat taagagaca
121  gccgcccgct ggtcctccct gaacttggct cagctgcggg ctgctccgg ttggaaacgc
181  caagccagct gcgtcctaat ccaaaagcca tgaacagcgg cgtgtgcctg tgcgtgctga
241  tggcggtact ggcggctggc gccctgacgc agccggtgcc tccgcagat cccgcgggct
301  ccgggctgca gcgggcagag gaggcgcccc gtaggcagct gagggtatcg cagagaacgg
361  atggcgagtc ccgagcgcac ctggcgccc tgctggcaag atacatccag caggcccgga
421  aagctccttc tggacgaatg tccatcgtta agaacctgca gaacctggac ccagccaca
481  ggataagtga ccgggactac atgggctgga tggattttgg ccgtcgcagt gccgaggagt
541  atgagtaccc ctctagagg acccagccgc catcagccca acggaagca acctcccaac
601  ccagaggagg cagaataaga aaacaatcac actcataact cattgtctgt ggagtttgac
661  attgtatgta tctatttatt aagttctcaa tgtgaaaaat gtgtctgtaa gattgtccag
721  tgcaaccaca cacctcacca gaattgtgca aatggaagac aaaatgtttt cttcatctgt
781  gactcctggt ctgaaaatgt tgttatgcta ttaaagtgat ttcattctga aaaaaaaaa
841  aaaaaaaaaa a
```

FIG. 6 cont.

SEQ ID NO. 6: (cDNA encoding SEQ ID NO. 4)

```
1   atgaacagcg gcgtgtgcct gtgcgtgctg atggcggtac tggcggctgg cgccctgacg
61  cagccggtgc ctcccgcaga tccgcgggc tccgggctgc agcgggcaga ggaggcgccc
121 cgtaggcagc tgagggtatc gcagagaacg gatggcgagt cccgagcgca cctgggcgcc
181 ctgctggcaa gatacatcca gcaggcccgg aaagctcctt ctggacgaat gtccatcgtt
241 aagaacctgc agaacctgga ccccagccac aggataagtg accgggacta catgggctgg
301 atggattttg gccgtcgcag tgccgaggag tatgagtacc cctcctag
``` f) SEQ ID NO. 7 (Human Peptide YY 1-36 amino acid sequence)

YPIKPEAPGEDA SPEELNRYYA SLRHYLNLVT RQRY g) PYY cDNA       SEQ ID NO. 8

```
  1 gccctggag gaactgaccc cactatcggt catgggcg agactaaatg tggcggttg
 61 tctttaatct gctgccaaga ggaaactcat tcaggcaagt tcagccctt atgaggaatt
121 ccctgtggt cacattccaa ttcctggacc tgctgccacc ctcagaactg catgctcctt
181 cttcagacctt tctaagaatg actcaggtca ttggtggagt gaagtcaaga tttccaactc
241 agtcacctga agagatggag ataccattca tggagctgga ggtcctgga gatttggaa
301 ttcagataac aagctaagat aaggagtttg cctacctctg tcctagagcg aagctgagc
361 cttgggcgcg cagcacacca caagtatctg ttactgtgtt ttgcagaagc ttcaggcggg
421 gatataagcc ccacaggaa agcgctgagc agaggaggcc tcagcttgac ctgcggcagt
481 gcagccttg ggacttccct cgccttccac ctcctgctcg tctgcttcac aagctatcgc
541 tatgctgttc gtgcgcaggc cgtggccgc cttgaccaca gtgcttctgg ccctgctcgt
601 ctgcctaggg gcgctggtcg acgcctaccc catcaaaccc gaggctcccc gcgaagacgc
661 ctcgccgag gagctgaacc gctactacgc ctccctgcgc cactacctca acctggtcac
721 ccggcagcgg tatggaaaa gagacggccc ggacacgctt cttccaaaa cgttcttccc
781 cgacggcgag gaccgcccg tcaggtgcgg gtcggaggcc ccagacctgt ggtgaggacc
841 cctgaggcct cctgggagat ctgccaacca cgcccacgtc attgcatac gcactccga
901 ccccagaaac ccggattctg cctcccgacg gcggcgtctg ggcagggttc gggtgcgcc
961 ctccgcccgc gtctcggtgc cccgccccc tgggctggag ggctgtgt ggtcttccc
1021 tggtcccaaa ataaagagca aattcacag aaaaaaaaa aaaaaaaa
```

SATIATION PEPTIDE ADMINISTRATION

RELATED APPLICATIONS

This application is a continuation of U.S. patent application U.S. Ser. No. 15/271,369, filed Sep. 21, 2016, which is a divisional of and claims priority under 35 U.S.C. § 120 to U.S. patent application U.S. Ser. No. 13/145,660, filed Oct. 31, 2011, which is a 35 U.S.C. § 371 National Phase Application of International Application No. PCT/US2010/021677, filed Jan. 21, 2010, which claims priority to U.S. Ser. No. 61/146,287, filed Jan. 21, 2009, all of which are incorporated herein in their entireties.

INTRODUCTION

Satiation gut peptides are secreted from the small intestine and colon in response to food intake. Penetrating from plasma through the blood-brain barrier, they act by activating specific receptors in the satiety center of the hypothalamus thus inducing satiation. The most important satiation gut peptides are Peptide YY, Glucagon-like Peptide 1, Oxyntomodulin, and Cholecystokinin. Acute supplemental therapy with satiation gut peptides reduces food intake and body weight in obese animal models as well as in lean and obese human subjects. Several clinical trials utilizing satiation peptide supplement therapy are currently under way. In these trials, the tested peptide is administered by iv injections 30 min prior to the meal. It is widely acknowledged that satiation gut peptides would not be effective through ingested oral administration since enzymes and acids in the gut would degrade them prior to reaching the blood.

DETAILED DESCRIPTION

The present application is based on the inventors' work toward establishing either a stable and longer term delivery of satiation gut peptides and/or administration of satiation gut peptides intended for targeting specific areas of the body which have now been identified as effecting an unexpectedly favorable satiation response. According to certain embodiments, the invention pertains to compositions and methods for treating obesity involving satiation gut peptide administration to the mouth of a subject for a predetermined dose and frequency. According to specific embodiment, the subject invention pertains to providing a long-term increase of satiation peptides in the saliva by targeting salivary gland with vectors, including, but not limited to, recombinant Adeno-associated viral (rAAV) vector, adenoviral vector, or other suitable vectors for transfection of cells in a human or non-human animal, harboring the respective gene, for introduction and expression in targeted cells.

In another embodiment, the invention pertains to a method of inducing satiation in a subject that includes applying to at least a portion of the mouth of the subject a composition comprising a satiation gut peptide at a time period prior to eating (pre-prandial). The time period may be 5 seconds or more. In a specific embodiment, the time period is 5-360 min prior to eating. In a more specific embodiment, the time period is 30-120 min prior to eating.

Another embodiment relates to a container that comprises a solid (e.g. powder), fluid or semi-fluid composition that comprises satiation gut peptide and a pharmaceutically acceptable carrier. In a specific embodiment the container comprises a nozzle for ejecting the composition into the mouth of a subject. The container may be under pressure and/or be equipped with a pump nozzle.

Another embodiment relates to a mouth applicable article loaded with a satiation gut peptide. The article may be chewing gum loaded with peptide; a lozenge (e.g. a dissolvable solid or semi-solid object intended to hold in the mouth for a period of time) loaded with peptide, or a permeable pouch or sponge loaded with peptide. The article is designed for extended delivery of peptide to the mouth and/or pharynx, as opposed to conventional oral administration that involves the immediate swallowing of a pill, table or fluid composition as is conventionally understood as oral administration. In particular, the article is designed for delivery to the tongue.

According to another embodiment, cells related to the mouth such as mucosal or salivary gland cells are transformed with vectors engineered to express and release a satiation gut peptide.

In a specific embodiment, the peptide is delivered to the mouth and/or pharynx to a subject according to a generally continuous time period of at least 5, 10, 15 or more seconds. In another embodiment, the delivery is for 0.1-120 mins, including any specific 0.1 minute increment within such range. In a specific embodiment, the inventors have found that administration of the peptide such that it is in prolonged contact with the tongue is optimal.

Figure 6:
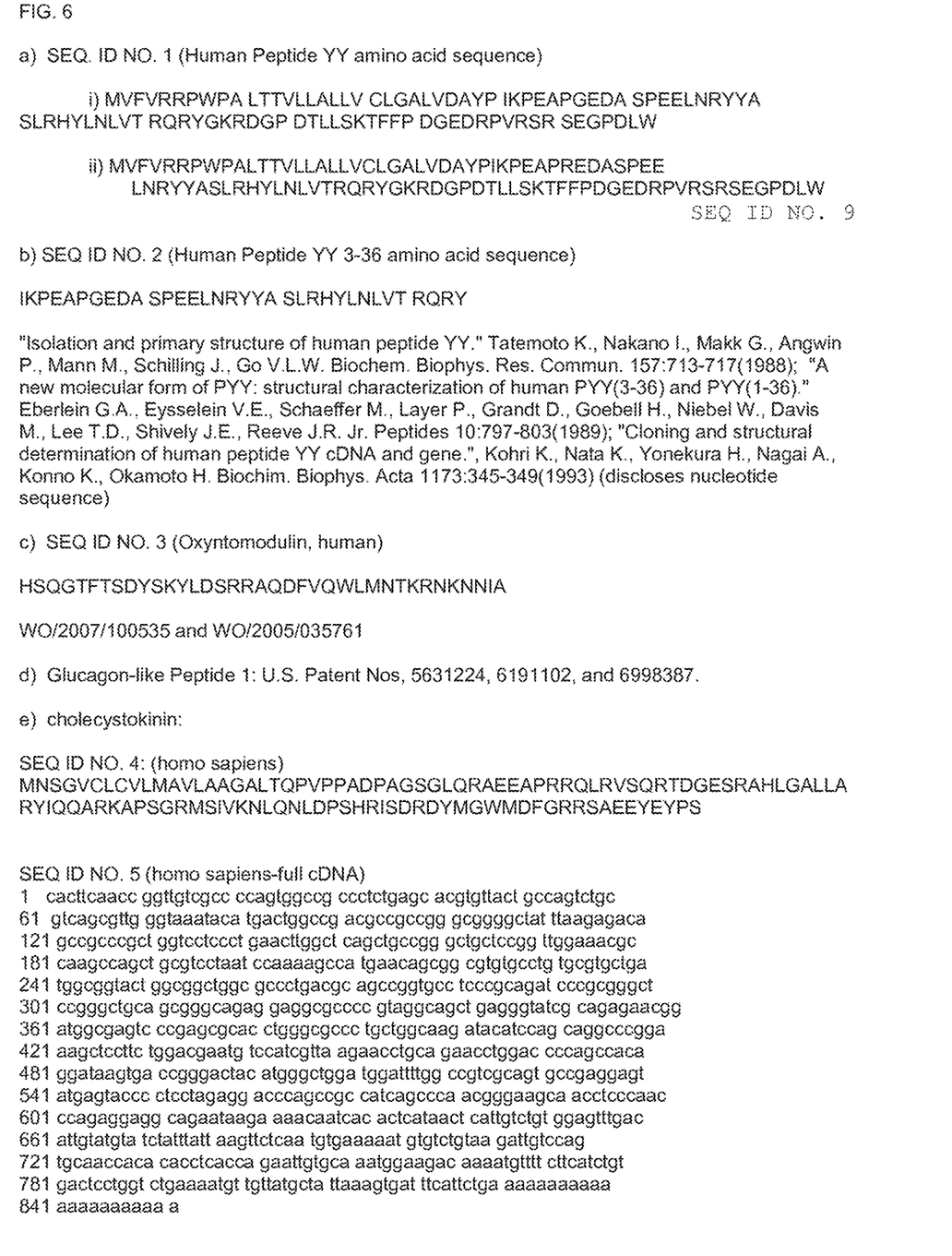
FIG. 6: shows example sequences pertaining to a) Human Peptide YY amino acid sequence, b) a portion of human PYY, c) Oxyntomodulin polypeptide, d) Glucagon-like Peptide 1, and e) cholecystokinin related sequences.

As described herein, the invention includes embodiments that utilize nucleotides encoding satiation gut peptides, or peptides alone. Satiation gut peptides include peptides relating to Peptide YY, Glucagon-like Peptide 1, Oxyntomodulin, and cholecystokinin. Nucleotides and peptides having substantial identity to the nucleotide and amino acid sequences relating to Peptide YY, Glucagon-like Peptide 1, Oxyntomodulin, and cholecystokinin also are contemplated for use in accordance with the teachings herein. Sequence information is provided in FIG. 6.

The proteins and polypeptide sequences, as well as polynucleotides encoding the same, having substantial identity with the sequences specifically described herein may be used in conjunction with present invention. Here "substantial identity" means that two sequences, when optimally aligned such as by the programs GAP or BESTFIT (peptides) using default gap weights, or as measured by computer algorithms BLASTX or BLASTP, share at least 50%, preferably at least 75%, and most preferably at least 95% sequence identity, or sequence identity of any integer percentage between 50% and 99.9%. Preferably, residue positions which are not identical differ by conservative amino acid substitutions. For example, the substitution of amino acids having similar chemical properties such as charge or polarity are not likely to effect the properties of a protein. Non-limiting examples include glutamine for asparagine or glutamic acid for aspartic acid.

The term "variant" as used herein refers to nucleotide and polypeptide sequences wherein the nucleotide or amino acid sequence exhibits substantial identity with the nucleotide or amino acid sequence SEQ ID NOS, preferably 75% sequence identity and most preferably 90-95% sequence identity to the sequences of the present invention: provided said variant has a biological activity as defined herein. The variant may be arrived at by modification of the native nucleotide or amino acid sequence by such modifications as insertion, substitution or deletion of one or more nucleotides or amino acids or it may be a naturally occurring variant. The term "variant" also includes homologous sequences which hybridise to the sequences of the invention under standard or preferably stringent hybridisation conditions familiar to those skilled in the art. Examples of the in situ hybridisation procedure typically used are described in (Tisdall et al., 1999); (Juengel et al., 2000). Where such a variant is desired, the nucleotide sequence of the native DNA is altered appropriately. This alteration can be made through elective synthesis of the DNA or by modification of the native DNA by, for example, site-specific or cassette mutagenesis. Preferably, where portions of cDNA or genomic DNA require sequence modifications, site-specific primer directed mutagenesis is employed, using techniques standard in the art.

In specific embodiments, a variant of a polypeptide is one having at least about 80% amino acid sequence identity with the amino acid sequence of a native sequence full length sequence of satiation gut peptides as taught herein and known in the art. Such variant polypeptides include, for instance, polypeptides wherein one or more amino acid residues are added, or deleted, at the N- and/or C-terminus, as well as within one or more internal domains, of the full-length amino acid sequence. Fragments of the peptides are also contemplated. Ordinarily, a variant polypeptide will have at least about 80% amino acid sequence identity, more preferably at least about 81% amino acid sequence identity, more preferably at least about 82% amino acid sequence identity, more preferably at least about 83% amino acid sequence identity, more preferably at least about 84% amino acid sequence identity, more preferably at least about 85% amino acid sequence identity, more preferably at least about 86% amino acid sequence identity, more preferably at least about 87% amino acid sequence identity, more preferably at least about 88% amino acid sequence identity, more preferably at least about 89% amino acid sequence identity, more preferably at least about 90% amino acid sequence identity, more preferably at least about 91% amino acid sequence identity, more preferably at least about 92% amino acid sequence identity, more preferably at least about 93% amino acid sequence identity, more preferably at least about 94% amino acid sequence identity, more preferably at least about 95% amino acid sequence identity, more preferably at least about 96% amino acid sequence identity, more preferably at least about 97% amino acid sequence identity, more preferably at least about 98% amino acid sequence identity and yet more preferably at least about 99% amino acid sequence identity with a polypeptide encoded by a nucleic acid molecule shown in Attachment B or a specified fragment thereof. Ordinarily, variant polypeptides are at least about 10 amino acids in length, often at least about 20 amino acids in length, more often at least about 30 amino acids in length, more often at least about 40 amino acids in length, more often at least about 50 amino acids in length, more often at least about 60 amino acids in length, more often at least about 70 amino acids in length, more often at least about 80 amino acids in length, more often at least about 90 amino acids in length, more often at least about 100 amino acids in length, or more.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to re-anneal when complementary strands are present in an environment below their melting temperature. The higher the degree of desired identity between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, are identified by those that: (1) employ low ionic strength and high temperature for washing, 0.015 M sodium chloride/0.0015 M sodium citrate/0.1% sodium dodecyl sulfate at 50° C.; (2) employ during hybridization a denaturing agent, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42 degrees C.; or (3) employ 50% formamide, 5× SSC (0.75 M NaCl, 0.075 M sodium citrate), 50 mM sodium phosphate (pH 6.8), 0.1% sodium pyrophosphate, 5.times. Denhardt's solution, sonicated salmon sperm DNA (50 μg/ml), 0.1% SDS, and 10% dextran sulfate at 42 degrees C., with washes at 42 degrees C. in 0.2×SSC (sodium chloride/sodium citrate) and 50% formamide at 55 degrees C., followed by a high-stringency wash consisting of 0.1×SSC containing EDTA at 55 degrees C.

"Moderately stringent conditions" are identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37.degree. C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50 degrees C. The skilled artisan will recognize how to adjust the temperature, ionic strength, etc. as necessary to accommodate factors such as probe length and the like.

An oral liquid formulation may, for example, be a pharmaceutically acceptable emulsion, syrup, elixir, suspension, solution and the like, which may contain a pharmaceutically customary inert diluent such as water and if desired, additives. Such an oral liquid formulation can be produced by mixing an active ingredient, inert diluent and other additives if necessary in accordance with a customary method. An oral formulation usually contain about 0.01 to 99% by weight, preferably about 0.1 to 90% by weight, usually about 0.5 to 50% by weight of an inventive active compound, although the amount may vary depending on the dosage form.

In certain embodiments, a formulation is prepared for spraying into the mouth. The composition may be placed in a container equipped with a sprayer nozzle and either ejected through a pump motion or by release of pressure.

In another embodiment, the composition is combined and provided in the form of a chewing gum.

Example 1

PYY Gene Therapy

Peptide YY (PYY) is a satiation gut peptide secreted from the neuro-endocrine L cells from the small intestine and colon epithelia. PYY is secreted into the blood stream and subsequently activates Y receptors in the arcuate nucleus of the hypothalamus thus inducing satiation. In the pilot study, in addition to the plasma, we have also detected PYY in saliva in naïve, untreated mice, while at the same time identifying the respective Y2 receptor in the tongue epithelia. To the inventors' knowledge, these are novel findings which lead to the following hypothesis: long-term expression of genes coding for satiation peptide in salivary gland will reduce food intake and body weight in obese animal.

Figure 1:
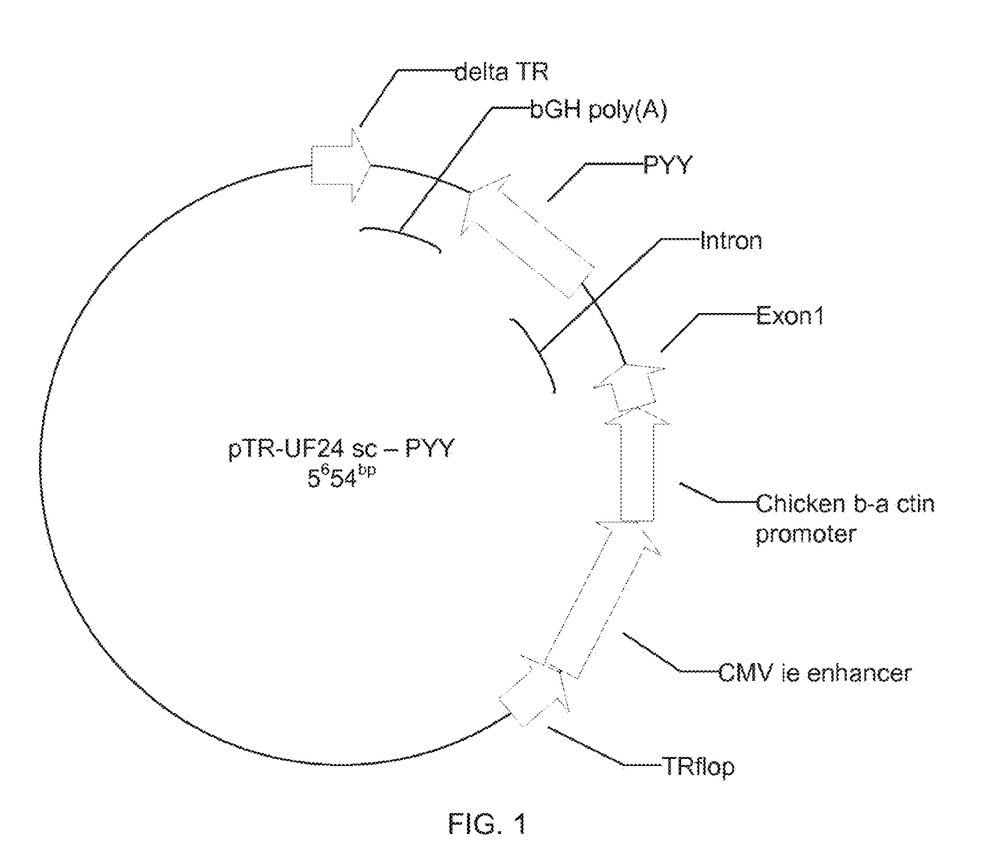
FIG. 1: rAAV-PYY vector plasmid: TR (terminal repeat), CMV (cytomegalovirus) enhancer, CBA (Chicken B actin) promoter.

In order to overexpress PYY, a rAAV vector was constructed harboring the pre-pro-Peptide YY gene (FIG. 1). rAAV-PYY was administered into the salivary glands through the salivary ducts. Injection of rAAV-PYY resulted in a long-term (up to 6 months) expression of Peptide YY as measured by the respective ELISA assay (not shown).

Figure 2:
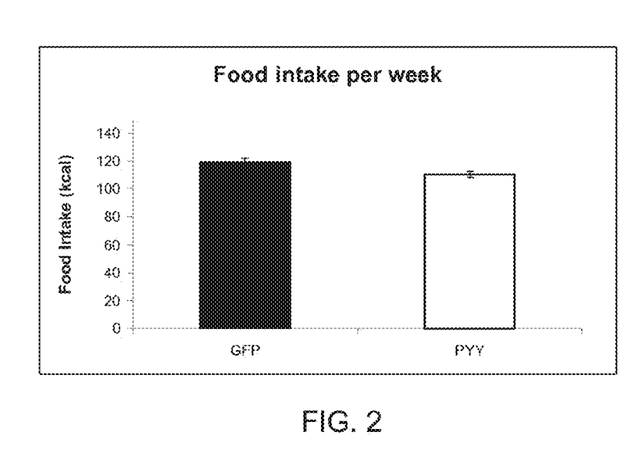
FIG. 2: Food intake per week in 8 months-old DIO mice injected with rAAV-PYY vs. rAAV-GFP *P<0.05
Figure 3:
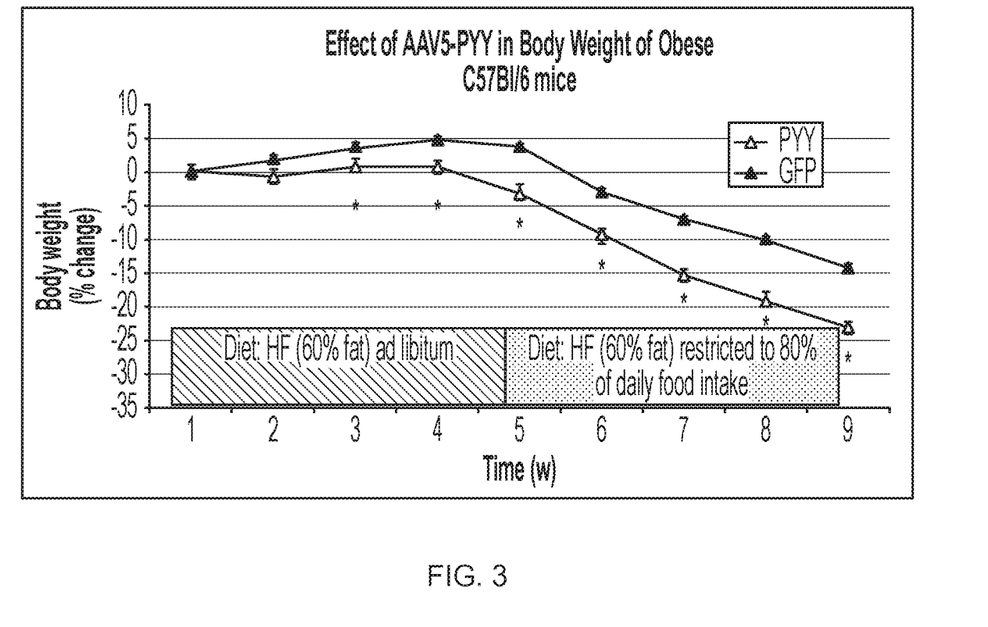
FIG. 3: Body weight change in 8 months-old diet-induced obese (DIO)-mice injected with rAAV-PYY vs. rAAV-GFP (controls). *P<0.05

The ectopic expression of PYY transgene in lean as well as in diet-induced obese mice produced a significant decrease in food intake and body weight compared to control group injected with reporter vector rAAV-GFP (FIGS. 2 and 3). The results of the inventors demonstrated that long-term expression of peptide YY transgene delivered by a viral vector is a viable therapy for the treatment of obesity.

Example 2

Long-Term Peptide YY Gene Therapy: Addressing Existing Controversy

Peptide YY (PYY) is a satiation gut hormone released postprandially mainly by the gut. The effects of acute and chronic administration of PYY are controversial. Several groups have found a significant decrease in food intake (FI) and body weight (BW) in animal experiments and in human trials, while other groups have been unable to reproduce this data. The controversy can be related to several behavioral factors including acclimatization and stress, as well as varying experimental conditions. To eliminate these factors and to address the effect of long-term overexpression of PYY we have develop animal models, C57BL/6 mice, with either homotopic or ectopic expression of pre-pro-PYY transgene delivered by a single injection of a viral vector. For the enhanced homotopic expression, the vector was delivered through superior mesenteric artery (SMA) to target the colon and small intestine where PYY is normally produced. For the ectopic expression, the vector had been delivered either into the $3^{rd}$ ventricle in the brain targeting hypothalamus, or into the salivary ducts to target submandibular salivary glands to induce PYY secretion in to saliva. All treated mice were fed high fat diet (60% fat) ad libitum, FI and BW were measured once a week for 30 weeks. In SMA-injected mice, we documented a sustained two-fold increase of PYY in plasma during fasting and ten-fold increase one hour after feeding. In spite of the significant increase of systemic PYY, no differences in BW or FI were documented at 30 weeks post-injection. On the contrary, in mice with PYY-encoding vector injected either centrally or in the salivary glands, the concentration of plasma PYY remained unchanged. However, centrally-injected mice exhibited significant increase in both BW and FI, while the long-term effect was opposite in salivary gland-treated animals. In satiation behavioral studies, neither treated group show a significant difference in FI after 16, or 24 hrs fasting. Our results suggest that the long-term overexpression of PYY have differential effect dependent on the targeted site. Physiological tests and hormonal profiles in mice from all groups will be presented and the possible mechanism of action of the exogenous PYY will be discussed.

Example 3

Administration of Satiation Gut Peptides to Mouth
Introduction

Satiation gut peptides are secreted into the bloodstream from the small intestine and colon in response to food intake (FI). Their main effect is to induce satiety by activation their specific receptors in the satiety center in the hypothalamus. The most important satiation gut peptides are Peptide YY (PYY), Glucagon-like Peptide 1 (GLP-1), Oxyntomodulin (OXM), and Cholecystokinin (CCK). Acute supplemental therapy with satiation gut peptides reduces FI and body weight (BW) in obese animal models as well as in lean and obese human subjects. Several clinical trials utilizing satiation peptide supplement therapy are currently under way. Unfortunately, the delivery methods of these peptides (iv injections) showed significant side effects and poor adherence. In the pilot study, in addition to the plasma, we have also detected PYY in saliva in naïve, untreated mice, while at the same time identifying the respective Y2 receptor in the tongue epithelia. Based on these novel findings, the inventors have developed a non-invasive, easy-to-use mouth spray to deliver these peptides. The aim is to reduce voluntary FI by inducing an early satiation effect mediated by an increased concentration of these peptides in the saliva. Incremental reduction in FI over the prolonged period of time will result in reduced BW and improved health.

Materials and Methods:

Synthetic PYY was purchased from Bachem, Inc USA (Cat #H-6042) and diluted in sterile $H_2O$. Sterile un-used perfume sample vials (Saphora) were utilized to administer PYY in the form of a mouth spray. It was estimated that the volume of one spray approximates to about 25 l.

Mice were conditioned three times to 24 hours fasting starting at the beginning of the dark cycle and ending at the end of the light cycle. At the end of the fasting cycle and as a part of conditioned routine, a sterile water spray had been administered into the mouth. All the experiments were done during the first hour of the dark cycle after fasting. Once the dark cycle started, mice were sprayed once with either PYY or sterile $H_2O$ in a total volume of 25 l per spray. After the treatment, mice were returned to their cages and ten minutes later pre-weighted chow was provided. One hour later, the amount of consumed chow had been recorded by measuring the leftover amount. When the experiments were repeated, mice were fasted only once a week with the control and experimental groups rotated.

Figure 4:
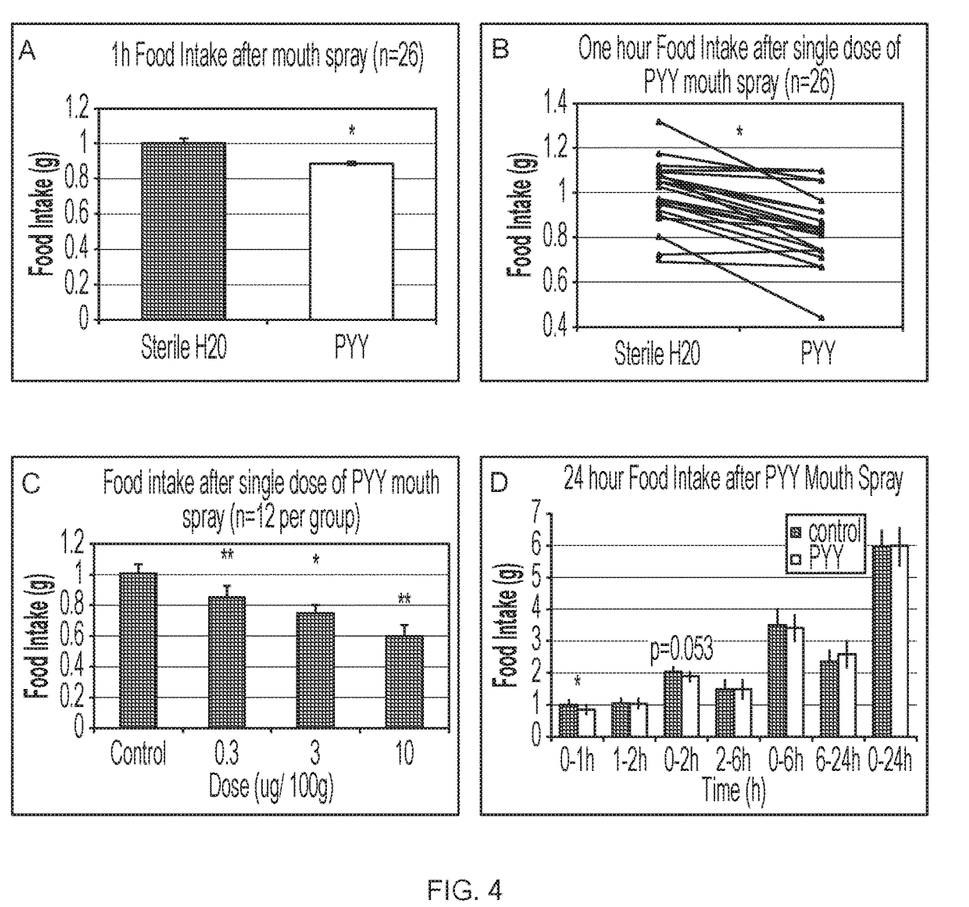
FIG. 4: Effects of Peptide YY Mouth Spray. A) One hour food intake after one spray with PYY, 5 ug per 100 g of body weight vs. spray with sterile $H_2O$. B) Difference in one hour food intake after PYY mouth spray vs. Sterile H2O, shown are individual animals. C) Dose response of PYY mouth spray on FI as measured after one hour. D) 24 hours food intake after PYY mouth spray vs. sterile $H_2O$. *P<0.05, **P<0.01.

Results:

Mice sprayed with PYY consumed significantly (P=0.03) less food (15% on average) compared to the control group sprayed with $H_2O$ (FIG. 4A, 4B). We also documented a significant PYY dose response effect to FI (FIG. 4C). After PYY mouth spray, there was a pronounced early satiety effect followed by compensatory higher food intake resulting in similar overall 24 hr period FI for both experimental and control groups (FIG. 4D). This data correlates with previously published observation showing no difference in FI during 24 hours after IP or IV injections. This data, however, reflect the ad libitum pattern of food consumption in mice. In humans, with a defined pattern of three meals per day, with PYY spray application prior to each meal, the treatment is anticipated to reduce overall FI over 24 hrs period.

Conclusions:

The increase in PYY concentration delivered by mouth spray has a potential to be utilized as a treatment for obesity by reducing voluntary FI. Attachment A in U.S. Provisional Application No. 61/146,287 sets forth data demonstrating the successful expression of Peptide YY and the use for modulating BMI and FI.

Example 4

Long-Term Salivary PYY3-36 Treatment Modulates Aggressive Behavior

The NPY pathway modulates food intake, body weight, energy expenditure, blood pressure, cortical excitability, circadian rhythms, stress response, emotions, memory, attention, learning, aggression, ethanol susceptibility and pain processing. The NPY pathway has also been related to the mechanism of epilepsy, neurogenesis, neuroprotection, analgesia, anxiety and depression (1, 2). The widespread effects of NPY are mediated by G-protein coupled receptors Y1, Y2, Y4, Y5 and Y6.

Components of the Neuropeptide Y (NPY) expressed widely in the CNS have been linked to aggression, anxiety and depression. For example, NPY Y1 and Y4 receptor knockout mice exhibit abnormally aggressive behavior (1). Furthermore, both pharmacological inhibition of NPY Y2 receptor and NPY Y2 receptor knockout show an anxiolytic, antidepressant phenotypes with reduced attention and increased impulsivity (3, 4) (5). However, so far little is known about the role of NPY Y2 receptors in aggressive behavior.

NPY Y2 receptors endogenous agonist is $PYY_{3-36}$. Recently, we reported that augmentation of salivary $PYY_{3-36}$ modifies feeding behavior in mice. The long-term increase of salivary $PYY_{3-36}$ by using a recombinant Adeno-associated virus (rAAV-PYY), produced a significant decrease in body weight and food intake in obese mice. Unexpectedly, in addition to modulating the feeding behavior, the long term over-expression of salivary $PYY_{3-36}$ also appears to modulate aggressive behavior.

Data presented in this report indicate that long-term expression of Peptide $YY_{3-36}$, an agonist of NPY Y receptors with higher affinity for the Y2 receptor, abolish aggressive behavior in mice. To test these observations, we used the territorial Resident/Intruder (R/I) aggressive paradigm (6), a standard test for evaluating rodent aggressive behavior. The test was applied on three different occasions using different intruders. Tests were recorded and analyzed in a blind manner using the Observer v5.0 software (Noldus Information Technology) (see videos, Supplementary data) (7).

Figure 5:
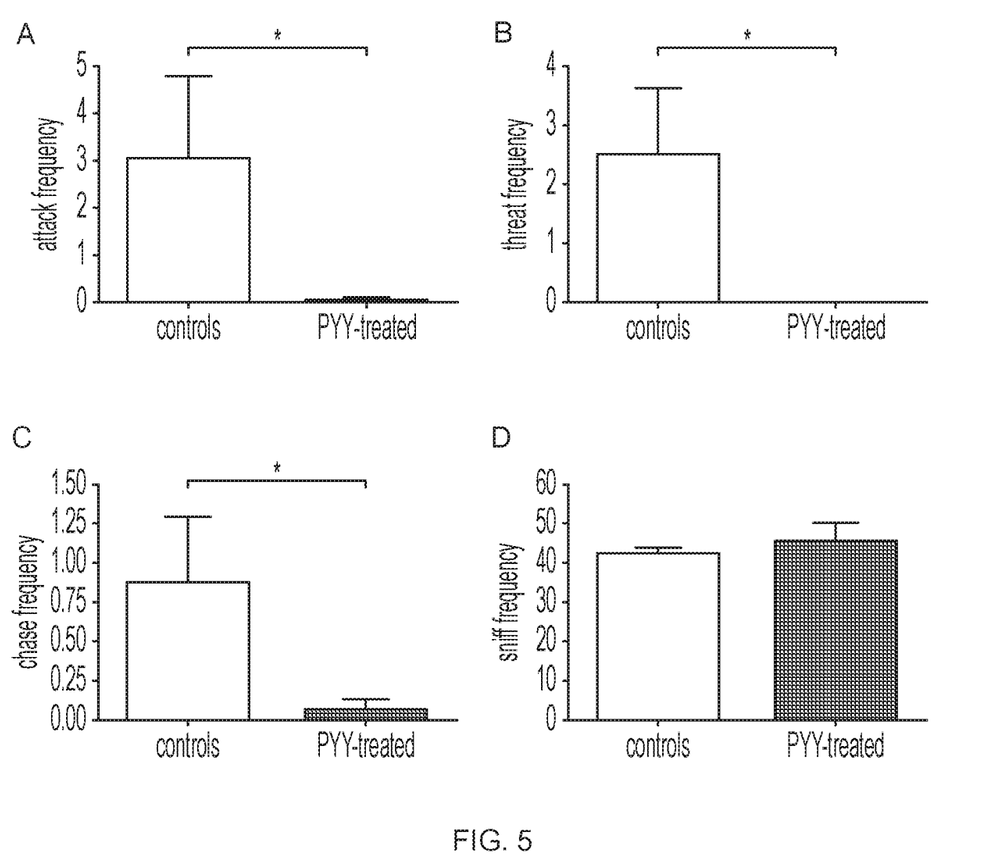
FIG. 5: relates to effects of extended PYY administration on behavior of mice concerning (A) attack frequency (B) threat frequency (C) chase frequency and (D) frequency.

The aggressive behavior was analyzed by the frequency, duration and latency of attacks, threats and chase from the resident to the intruder mice. $PYY_{3-36}$ treated mice displayed a 44-fold decrease in the number of attack events compare to controls [$PYY_{3-36}$ 0.07±0.067 events per 10 min, vs. Controls 3.07±1.74 events in 10 min, n=5, p<0.05) (FIG. 5A). Likewise, $PYY_{3-36}$ treated mice had a significant decrease in attack duration and a significant increase in attack latency. Similarly, $PYY_{3-36}$ treated mice had a significant decrease in threat events and duration compare to controls (FIG. 5B) and a decrease in chase events and duration compare to control mice (FIG. 5C). Interestingly, even though an aggressive behavior was almost completely abrogated, the normal social interactions manifested by sniffing did not change (FIG. 5D).

These dramatic changes in territorial aggression suggest that the long-term treatment with NPY Y2 receptors agonists such as $PYY_{3-36}$ modulates both feeding and aggressive behaviors. Because $PYY_{3-36}$ has recently been tested in clinical trials for weight loss in obese adult subjects, the unintended while favorable effects shown here must be taken in consideration before such agonists are approved for the long-term treatment of obesity. This is especially important in light of the Y receptors cross talk and interactions as shown in genetically modified mice models (8). Further studies are needed to understand the long-term effect of Y receptors agonists in feeding and aggressive behavior, as well as in depression and anxiety.

Supplemental Material:

Methods

Vector design: A recombinant adeno-associated virus encoding murine pre-pro-PYY (rAAV-PYY) under the control of a strong constitutive CMV/-actin promoter and the control rAAV-GFP were pseudotyped into rAAV serotype 5 capsids as having higher transduction in salivary glands (SG) (9). The production, purification and titration of the viral vectors were performed as described previously (10).

Mouse studies: This study was approved by the Animals Care and Use Committee of The National Institute of Dental and Craniofacial research and by the Biosafety Committee of the National Institute of Health (Bethesda, Md.). All mice procedures were done in accordance with the principles of the National Research Council's guide for the Care and Use of Laboratory Animals. Studies were done in male Balb/c (Harlan Sprague Dawley, Walkersville, Md.) mice housed at 22-24° C. in a 12 hours light/dark cycle (lights off at 1800). Forty five days old male Balb/C mice (n=5) were administered a single dose of (100 I, $10^{10}$ vector genomes) rAAV-PYY, rAAV-GFP or saline control bi-laterally into the orifice of the submandibular salivary gland as described by Katano et al (9).

Metabolic profile: Mice had free access to water and food (normal chow). Food intake and body weight were measured weekly for 24 weeks.

Behavioral studies: Aggression territorial-Intruder test were performed on week 24 after the treatment (6). Briefly, PYY-, or GFP-treated resident mice were individually housed for at least two weeks prior to testing. Bedding from cages was not changed during the testing period to avoid unnecessary stress. On the day of the experiment, a smaller size intruder was placed into the resident cage for 10 minutes and the resident's behavior was recorded with a video camera. Each experiment was repeated 3 times on three different occasions and with different intruders. The videos from the experiments were analyzed for non-aggressive and aggressive behavior by an expert in a blind manner using The Observer v5.0 software (Noldus Information Technology) (7).

Statistical analysis: Statistical analysis was conducted using un-paired Student's t-test or by a Mann-Whitney test with significance at P<0.05. Data was reported in mean±SEM.

Results:

Metabolic Profile: rAAV-PYY treated mice weekly caloric intake was significantly lower than rAAV-GFP control mice (rAAV-PYY 95.53±2.35 kcal vs. rAAV-GFP 107.44±3.22 kcal, p<0.002). Twenty two weeks after vector delivery, the rAAV-PYY treated mice gained significantly less weight than the controls mice (rAAV-PYY 5.33±0.63 g vs. rAAV-GFP 6.28±0.68 g, p<0.05). These data suggest that long-term chronic elevation of $PYY_{3-36}$ in saliva of lean mice modulates feeding behavior by decreasing food intake and body weight.

REFERENCES CITED FOR EXAMPLE 4

1. T. Karl, H. Herzog. *Peptides* 28, 326 (February 2007).
2. E. E. Benarroch, *Neurology* 72, 1016 (Mar. 17, 2009, 2009).
3. A. Tschenett et al., *Eur J Neurosci* 18, 143 (July 2003).
4. J. P. Redrobe, Y. Dumont, H. Herzog, R. Quirion, *Behav Brain Res* 141, 251 (May 15, 2003).
5. B. Greco, M. Carli, *Behav Brain Res* 169, 325 (May 15, 2006).
6. T. Karl et al., *Proc Natl Acad Sci USA* 101, 12742 (Aug. 24, 2004).
7. A. M. Muehlmann, B. D. Brown, D. P. Devine, *J Pharmacol Exp Ther* 324, 214 (Jan. 1, 2008, 2008).
8. W. Wittmann, S. Loacker, I. Kapeller, H. Herzog, C. Schwarzer, *Neuroscience* 136, 241 (2005).
9. H. Katano et al., *Gene Ther* 13, 594 (April 2006).
10. S. Zolotukhin et al., *Methods* 28, 158 (October 2002).

The teachings of the references cited throughout the specification are incorporated herein in their entirety by this reference to the extent they are not inconsistent with the teachings herein. It should be understood that the examples and the embodiments described herein are for illustrative purposes only and that various modifications or changes in light thereof will be suggested to persons skilled in the art and are to be included within the spirit and purview of this application.

What is claimed is:

1. A mouth-applicable article designed for delivery of a pharmaceutical composition to the tongue of a subject in need thereof, wherein the article comprises a composition that comprises Peptide YY (PYY) in a unit dosage form, wherein the unit dosage form provides satiation in the subject and provides no substantial change to the concentration of PYY in the plasma of the subject after the delivery, and wherein the mouth-applicable article comprises a chewing gum or a lozenge that comprises a dissolvable planar sheet or a solid or semi-solid object.

2. The mouth-applicable article of claim 1, wherein said PYY has at least about 95% amino acid sequence identity with the full-length amino acid sequence of PYY.

3. The mouth-applicable article of claim 1, wherein said PYY is $PYY_{3-36}$.

4. The mouth-applicable article of claim 3, wherein said PYY has the amino acid sequence of SEQ ID NO. 2.

5. The mouth-applicable article of claim 1, wherein said lozenge comprises a solid or semi-solid object.

6. The mouth-applicable article of claim 1, wherein said lozenge comprises a dissolvable planar sheet.

7. The mouth-applicable article of claim 1, wherein said mouth-applicable article is a chewing gum.

8. The mouth-applicable article of claim 1, wherein said composition contains about 0.5 to 50% by weight of PYY.

9. The mouth-applicable article of claim 1, wherein the article provides delivery of the composition at a dosage in a range of about 0.3 µg per 100 g of body weight to 10 µg per 100 g of body weight.

10. The mouth-applicable article of claim 9, wherein the article provides delivery of said composition at a dosage of about 5 µg per 100 g of body weight.

11. The mouth-applicable article of claim 1, wherein the therapeutically effective dose does not substantially change the concentration of PYY in the plasma of the subject when the PYY is applied to the tongue of the subject at a time period prior to eating.

12. The mouth-applicable article of claim 11, wherein the time period is 5-360 seconds.

13. The mouth-applicable article of claim 11, wherein the time period is 5 seconds or more.

14. The mouth-applicable article of claim 13, wherein the time period is about 30-120 minutes.

15. The mouth-applicable article of claim 1, wherein the article is designed for extended delivery of the PYY to the tongue for a defined time period.

16. The mouth-applicable article of claim 15, wherein the defined time period is at least 5 seconds.

17. The mouth-applicable article of claim 15, wherein the defined time period is about 0.1 to 120 minutes.

18. The mouth-applicable article of claim 1, wherein said mouth-applicable article is designed for delivery at least 30 minutes prior to eating.

19. The mouth-applicable article of claim 18, wherein said mouth-applicable article is designed for delivery 30-120 minutes prior to eating.

20. A mouth-applicable article designed for delivery of a pharmaceutical composition to the tongue of a subject in need thereof, wherein the article comprises a composition that comprises Peptide YY (PYY) and a pharmaceutically acceptable emulsion, syrup, or elixir in a unit dosage form, wherein the unit dosage form provides satiation in the subject and provides no substantial change to the concentration of PYY in the plasma of the subject after the delivery, and wherein the mouth-applicable article comprises a liquid in a form of a spray or drops, or wherein the mouth-applicable article comprises a semi-fluid in a form of drops.

21. The mouth-applicable article of claim 20, wherein the article provides delivery of the liquid of a spray form at a dosage of about 5 µg per 100 g of body weight.

22. A container comprising the mouth-applicable article of claim 20.

23. The container of claim 22, further comprising a nozzle for ejecting the mouth-applicable article into the mouth of a subject.

24. The container of claim 22, wherein the container is under pressure.

25. The container of claim 22, wherein the mouth-applicable article comprises a semi-fluid composition in a form of drops.

26. A method of inducing satiation in a subject, comprising applying a therapeutically effective dose of the mouth applicable article of claim 1 to the tongue of said subject.

27. A method of treating obesity in a subject, comprising administering a therapeutically effective dose of the mouth applicable article of claim 1 to the subject.

\* \* \* \* \*

SEQUENCE LISTING

```
<160> NUMBER OF SEQ ID NOS: 9

<210> SEQ ID NO 1
<211> LENGTH: 97
<212> TYPE: PRT
<213> ORGANISM: Homo sapiens

<400> SEQUENCE: 1

Met Val Phe Val Arg Arg Pro Trp Pro Ala Leu Thr Thr Val Leu Leu
1               5                   10                  15

Ala Leu Leu Val Cys Leu Gly Ala Leu Val Asp Ala Tyr Pro Ile Lys
            20                  25                  30

Pro Glu Ala Pro Gly Glu Asp Ala Ser Pro Glu Glu Leu Asn Arg Tyr
        35                  40                  45

Tyr Ala Ser Leu Arg His Tyr Leu Asn Leu Val Thr Arg Gln Arg Tyr
    50                  55                  60

Gly Lys Arg Asp Gly Pro Asp Thr Leu Leu Ser Lys Thr Phe Phe Pro
65                  70                  75                  80

Asp Gly Glu Asp Arg Pro Val Arg Ser Arg Ser Glu Gly Pro Asp Leu
                85                  90                  95

Trp

<210> SEQ ID NO 2
<211> LENGTH: 34
<212> TYPE: PRT
<213> ORGANISM: Homo sapiens

<400> SEQUENCE: 2

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
```

```
<210> SEQ ID NO 3
<211> LENGTH: 37
<212> TYPE: PRT
<213> ORGANISM: Homo sapiens

<400> SEQUENCE: 3

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Lys Asn Asn Ile Ala
        35

<210> SEQ ID NO 4
<211> LENGTH: 115
<212> TYPE: PRT
<213> ORGANISM: Homo sapiens

<400> SEQUENCE: 4

Met Asn Ser Gly Val Cys Leu Cys Val Leu Met Ala Val Leu Ala Ala
1               5                   10                  15

Gly Ala Leu Thr Gln Pro Val Pro Pro Ala Asp Pro Ala Gly Ser Gly
            20                  25                  30

Leu Gln Arg Ala Glu Glu Ala Pro Arg Arg Gln Leu Arg Val Ser Gln
            35                  40                  45

Arg Thr Asp Gly Glu Ser Arg Ala His Leu Gly Ala Leu Leu Ala Arg
    50                  55                  60

Tyr Ile Gln Gln Ala Arg Lys Ala Pro Ser Gly Arg Met Ser Ile Val
65                  70                  75                  80

Lys Asn Leu Gln Asn Leu Asp Pro Ser His Arg Ile Ser Asp Arg Asp
                85                  90                  95

Tyr Met Gly Trp Met Asp Phe Gly Arg Arg Ser Ala Glu Glu Tyr Glu
            100                 105                 110

Tyr Pro Ser
        115

<210> SEQ ID NO 5
<211> LENGTH: 851
<212> TYPE: DNA
<213> ORGANISM: Homo sapiens

<400> SEQUENCE: 5
cacttcaacc ggttgtcgcc ccagtggccg ccctctgagc acgtgttact gccagtctgc      60
gtcagcgttg ggtaaataca tgactggccg acgccgccgg gcggggctat ttaagagaca     120
gccgcccgct ggtcctccct gaacttggct cagctgccgg gctgctccgg ttggaaacgc     180
caagccagct gcgtcctaat ccaaaagcca tgaacagcgg cgtgtgcctg tgcgtgctga     240
tggcggtact ggcggctggc gccctgacgc agccggtgcc tcccgcagat cccgcgggct     300
ccgggctgca gcgggcagag gaggcgcccc gtaggcagct gagggtatcg agagaacgg      360 atggcgagtc ccgagcgcac ctgggcgccc tgctggcaag atacatccag caggcccgga     420
aagctccttc tggacgaatg tccatcgtta gaacctgca gaacctggac ccagccaca      480 ggataagtga ccgggactac atgggctgga tggattttgg ccgtcgcagt gccgaggagt     540
```

```
atgagtaccc ctcctagagg acccagccgc catcagccca acgggaagca acctcccaac    600
ccagaggagg cagaataaga aaacaatcac actcataact cattgtctgt ggagtttgac    660
attgtatgta tctatttatt aagttctcaa tgtgaaaaat gtgtctgtaa gattgtccag    720
tgcaaccaca cacctcacca gaattgtgca aatggaagac aaaatgtttt cttcatctgt    780
gactcctggt ctgaaaatgt tgttatgcta ttaaagtgat ttcattctga aaaaaaaaa    840 aaaaaaaaaa a                                                         851
```

<210> SEQ ID NO 6
<211> LENGTH: 348
<212> TYPE: DNA
<213> ORGANISM: Homo sapiens

<400> SEQUENCE: 6

```
atgaacagcg gcgtgtgcct gtgcgtgctg atggcggtac tggcggctgg cgccctgacg     60
cagccggtgc ctcccgcaga tcccgcgggc tccgggctgc agcgggcaga ggaggcgccc    120
cgtaggcagc tgagggtatc gcagagaacg gatggcgagt cccagcgcca cctgggcgcc    180
ctgctggcaa gatacatcca gcaggcccgg aaagctcctt ctggacgaat gtccatcgtt    240
aagaacctgc agaacctgga ccccagccac aggataagtg accgggacta catgggctgg    300
atggattttg ccgtcgcag tgccgaggag tatgagtacc cctcctag                  348
```

<210> SEQ ID NO 7
<211> LENGTH: 36
<212> TYPE: PRT
<213> ORGANISM: Homo sapiens

<400> SEQUENCE: 7

```
Tyr Pro Ile Lys Pro Glu Ala Pro Gly Glu Asp Ala Ser Pro Glu Glu
 1               5                  10                  15

Leu Asn Arg Tyr Tyr Ala Ser Leu Arg His Tyr Leu Asn Leu Val Thr
            20                  25                  30

Arg Gln Arg Tyr
        35
```

<210> SEQ ID NO 8
<211> LENGTH: 1069
<212> TYPE: DNA
<213> ORGANISM: Homo sapiens

<400> SEQUENCE: 8

```
gcccctggag gaactgaacc cactatcggt catggggccg agactaaatg tggcgggttg     60
tctttaatct gctgccaaga ggaaactcat tcaggcaagt tcagcccttt atgaggaatt    120
cccctgtggt cacattccaa ttcctggacc tgctgccacc ctcagaactg catgctcctt    180
cttcagactt tctaagaatg actcaggtca ttggtggagt gaagtcaaga tttccaactc    240
agtcacctga agagatggag ataccattca tggagctgga ggtccctgga gatttgggaa    300
ttcagataac aagctaagat aaggagtttg cctacctctg tcctagagcg aagcctgagc    360
cttgggcgcg cagcacacca caagtatctg ttactgtgtt ttgcagaagc ttcaggcggg    420
gatataagcc ccacaaggaa agcgctgagc agaggaggcc tcagcttgac ctgcggcagt    480
gcagcccttg ggacttccct cgccttccac ctcctgctcg tctgcttcac aagctatcgc    540
tatggtgttc gtcgcaggc cgtggcccgc cttgaccaca gtgcttctgg ccctgctcgt    600
ctgcctaggg gcgctggtcg acgcctaccc catcaaaccc gaggctcccc gcgaagacgc    660
```

-continued

```
ctcgccggag gagctgaacc gctactacgc ctccctgcgc cactacctca acctggtcac    720
ccggcagcgg tatgggaaaa gagacggccc ggacacgctt ctttccaaaa cgttcttccc    780
cgacggcgag gaccgccccg tcaggtcgcg gtcggagggc ccagacctgt ggtgaggacc    840
cctgaggcct cctgggagat ctgccaacca cgcccacgtc atttgcatac gcactcccga    900
ccccagaaac ccggattctg cctcccgacg gcggcgtctg ggcagggttc gggtgcggcc    960
ctccgcccgc gtctcggtgc ccccgccccc tgggctggag ggctgtgtgt ggtccttccc   1020
tggtcccaaa ataaagagca aattccacag aaaaaaaaaa aaaaaaaa                1069
```

<210> SEQ ID NO 9
<211> LENGTH: 97
<212> TYPE: PRT
<213> ORGANISM: Homo sapiens

<400> SEQUENCE: 9

```
Met Val Phe Val Arg Arg Pro Trp Pro Ala Leu Thr Thr Val Leu Leu
1               5                   10                  15

Ala Leu Leu Val Cys Leu Gly Ala Leu Val Asp Ala Tyr Pro Ile Lys
                20                  25                  30

Pro Glu Ala Pro Arg Glu Asp Ala Ser Pro Glu Glu Leu Asn Arg Tyr
            35                  40                  45

Tyr Ala Ser Leu Arg His Tyr Leu Asn Leu Val Thr Arg Gln Arg Tyr
        50                  55                  60

Gly Lys Arg Asp Gly Pro Asp Thr Leu Leu Ser Lys Thr Phe Phe Pro
65                  70                  75                  80

Asp Gly Glu Asp Arg Pro Val Arg Ser Arg Ser Glu Gly Pro Asp Leu
                85                  90                  95

Trp
```